United States Patent
Habuka et al.

(10) Patent No.: US 11,014,814 B2
(45) Date of Patent: May 25, 2021

(54) VANADIUM NITRIDE FILM, AND MEMBER COATED WITH VANADIUM NITRIDE FILM AND METHOD FOR MANUFACTURING THE SAME

(71) Applicant: DOWA THERMOTECH CO., LTD., Tokyo (JP)

(72) Inventors: Satoru Habuka, Aichi (JP); Hiroyuki Matsuoka, Aichi (JP); Wataru Sakakibara, Aichi (JP)

(73) Assignee: DOWA THERMOTECH CO., LTD., Tokyo (JP)

( * ) Notice: Subject to any disclaimer, the term of this patent is extended or adjusted under 35 U.S.C. 154(b) by 140 days.

(21) Appl. No.: 16/319,604

(22) PCT Filed: Jul. 27, 2017

(86) PCT No.: PCT/JP2017/027222
§ 371 (c)(1),
(2) Date: Jan. 22, 2019

(87) PCT Pub. No.: WO2018/021466
PCT Pub. Date: Feb. 1, 2018

(65) Prior Publication Data
US 2020/0198967 A1 Jun. 25, 2020

(30) Foreign Application Priority Data
Jul. 27, 2016 (JP) .............. JP2016-146948

(51) Int. Cl.
| | | |
|---|---|---|
| C01B 21/06 | (2006.01) |
| B23B 27/14 | (2006.01) |
| C23C 16/34 | (2006.01) |
| C23C 16/50 | (2006.01) |
| C23C 16/52 | (2006.01) |
| C23C 16/36 | (2006.01) |
| C22C 38/24 | (2006.01) |
| C22C 38/46 | (2006.01) |
| C23C 14/06 | (2006.01) |

(52) U.S. Cl.
CPC ........ *C01B 21/0617* (2013.01); *B23B 27/148* (2013.01); *C22C 38/24* (2013.01); *C22C 38/46* (2013.01); *C23C 14/0647* (2013.01); *C23C 14/0652* (2013.01); *C23C 16/34* (2013.01); *C23C 16/347* (2013.01); *C23C 16/36* (2013.01); *C23C 16/50* (2013.01); *C23C 16/52* (2013.01); *B23B 2228/105* (2013.01); *C01P 2002/54* (2013.01); *C07C 2523/22* (2013.01); *C07C 2527/198* (2013.01)

(58) Field of Classification Search
CPC .............. C01B 21/0617; B23B 27/148; B23B 2228/105; C23C 16/50; C23C 16/52; C23C 16/34; C23C 16/347; C23C 16/36; C23C 14/0647; C23C 14/0652; C01P 2002/54; C22C 38/24; C22C 38/46; C07C 2523/22; C07C 2527/198
USPC ........... 106/286.1, 286.2, 287.27, 287.3, 286
See application file for complete search history.

(56) References Cited

U.S. PATENT DOCUMENTS
2013/0309876 A1  11/2013  Ogawa

FOREIGN PATENT DOCUMENTS
| | | |
|---|---|---|
| JP | 2002-011605 | 1/2002 |
| JP | 2002-371352 | 12/2002 |
| JP | 2004-323493 | 11/2004 |
| JP | 2005-46975 | 2/2005 |
| JP | 2010-202948 | 9/2010 |
| WO | 2012/073938 | 6/2012 |

OTHER PUBLICATIONS

Winter, et al. [Mat. Res. Soc. Symp. Proc. vol 327, pp. 109-113, 1994] (Winter) (Year: 1994).*
Nobuo Kieda et al., "Preparation of vanadium nitride films by CVD", Yogyo Kyokai Nenkai Koen Yokoshu, vol. 1987, No. 2, May 1987, pp. 557-558 (A concise explanation of the relevance is provided in the International Search Report in International Patent Application No. PCT/JP2017/027222, dated Sep. 5, 2017).
Ivan P. Parkin et al., "Atmospheric pressure chemical vapour deposition of vanadium nitride and oxynitride films on glass from reaction of VCl4 with NH3", Journal of Materials Chemistry, vol. 11, No. 12, Dec. 2001, pp. 3120-3124.
International Search Report in International Patent Application No. PCT/JP2017/027222, dated Sep. 5, 2017, along with an English translation thereof.
International Preliminary Report on Patentability in International Patent Application No. PCT/JP2017/027222, dated Jan. 29, 2019, along with an English translation thereof.

* cited by examiner

*Primary Examiner* — Elizabeth D Wood
(74) *Attorney, Agent, or Firm* — Greenblum & Bernstein, P.L.C.

(57) ABSTRACT

In a vanadium nitride film formed on a surface of a base material, a ratio V [at %]/N [at %] between a vanadium element concentration and a nitrogen element concentration in the film is 1.08 or more and a chlorine element concentration in the film is 1 at % or more and 5 at % or less.

4 Claims, 2 Drawing Sheets

VANADIUM NITRIDE FILM, AND MEMBER COATED WITH VANADIUM NITRIDE FILM AND METHOD FOR MANUFACTURING THE SAME

TECHNICAL FIELD

The present invention relates to a vanadium nitride film formed on a surface of a base material, and a coated member coated with the vanadium nitride film and a method for manufacturing the same.

BACKGROUND ART

Conventionally, the formation of a vanadium nitride film high in film hardness and rich in lubricity has been performed as a hard coating treatment on the surface of a die of press forming, a cutting tool, a gear cutting tool, a forging tool and so on.

As such a method for manufacturing the conventional vanadium nitride film, a method for forming a vanadium nitride film by the arc ion plating method is disclosed in Patent Document 1. Patent Document 1 discloses a vanadium nitride film having a Vickers hardness of about 2000. Further, Patent Document 2 also discloses a method for forming a vanadium nitride film by the ion plating method. Patent Document 2 discloses a vanadium nitride film having a Vickers hardness HV of about 2300.

PRIOR ART DOCUMENT

Patent Document

Patent Document 1: Japanese Laid-open Patent Publication No. 2002-371352
Patent Document 2: Japanese Laid-open Patent Publication No. 2005-46975

SUMMARY OF THE INVENTION

Problems to be Solved by the Invention

Normally, a harder coating is richer in abrasion resistance, but the hardness of the conventional vanadium nitride film has been about HV 2300. Accordingly, it has been required to form a vanadium nitride film having higher hardness for improvement of abrasion resistance.

A vanadium nitride film and a member coated with a vanadium nitride film according to the present invention have been made in consideration of the above circumstances and an object thereof is to improve the hardness of the vanadium nitride film.

Besides, as the conventional film formation method of the vanadium nitride film, a physical vapor deposition method represented by the ion plating has been used, arid therefore there is a need to take measures to the film formation apparatus such as provision of a rotation mechanism at a work table in the film formation processing on a complicated shape article such as a die because of poor throwing power of evaporating particles. Therefore, for the conventional film formation method of the vanadium nitride film, a film formation apparatus of special specifications for the film formation for the complicated shape article needs to be prepared, bringing about a problem of an increase in cost accompanying the introduction of the film formation apparatus. On the other hand, as the film formation method excellent in throwing power, the plasma chemical vapor deposition method is known. However, there is not any known method for manufacturing a vanadium nitride film using the plasma chemical vapor deposition method, and it has been completely unclear whether the plasma chemical vapor deposition method can improve the hardness of the vanadium nitride film and, in the first place, whether the plasma chemical vapor deposition method can be used for manufacture of the vanadium nitride film as a hard coating.

A method for manufacturing a member coated with a vanadium nitride film according to the present invention has been made in consideration of the problem and the aforementioned problems regarding the abrasion resistance of the vanadium nitride film, and an object thereof is to improve the hardness of the vanadium nitride film and to suppress the cost accompanying the introduction of the film formation apparatus.

Means for Solving the Problems

The present inventors have focused attention on the ratio between a vanadium element concentration [at %] and a nitrogen element concentration [at %] in the vanadium nitride film, and have found that when the ratio is 1.08 or more, the hardness of the vanadium nitride film improves. More specifically, the present invention solving the above problem is a vanadium nitride film formed on a surface of a base material, wherein a ratio V [at %]/N [at %] between a vanadium element concentration and a nitrogen element concentration in the film is 1.08 or more and a chlorine element concentration in the film is 1 at % or more and 5 at % or less. Note that the "vanadium nitride film" means a film composed of a compound containing vanadium and nitrogen as main components, and an example thereof is a film of a compound expressed by a chemical formula such as VN, $V_2N$, $VN_{0.81}$.

The present invention according to another aspect is a member coated with a vanadium nitride film, wherein a vanadium nitride film having a ratio V [at %]/N [at %] between a vanadium element concentration and a nitrogen element concentration of 1.08 or more and a chlorine element concentration of 1 at % or more and 5 at % or less is formed on a surface of a base material.

The present invention according to still another aspect is a method for manufacturing a member coated with a vanadium nitride film, the method including: supplying a raw material gas containing a nitrogen source gas, a vanadium chloride gas, and a hydrogen gas in forming the vanadium nitride film on a surface of a base material; and forming a vanadium nitride film having a ratio V [at %]/N [at %] between a vanadium element concentration and a nitrogen element concentration of 1.08 or more and a chlorine element concentration of 1 at % or more and 5 at % or less on the surface of the base material by a plasma chemical vapor deposition method.

Effect of the Invention

According to the present invention, it is possible to obtain a vanadium nitride film improved in hardness as compared with the conventional one.

MODES FOR CARRYING OUT INVENTION

Figure 1:
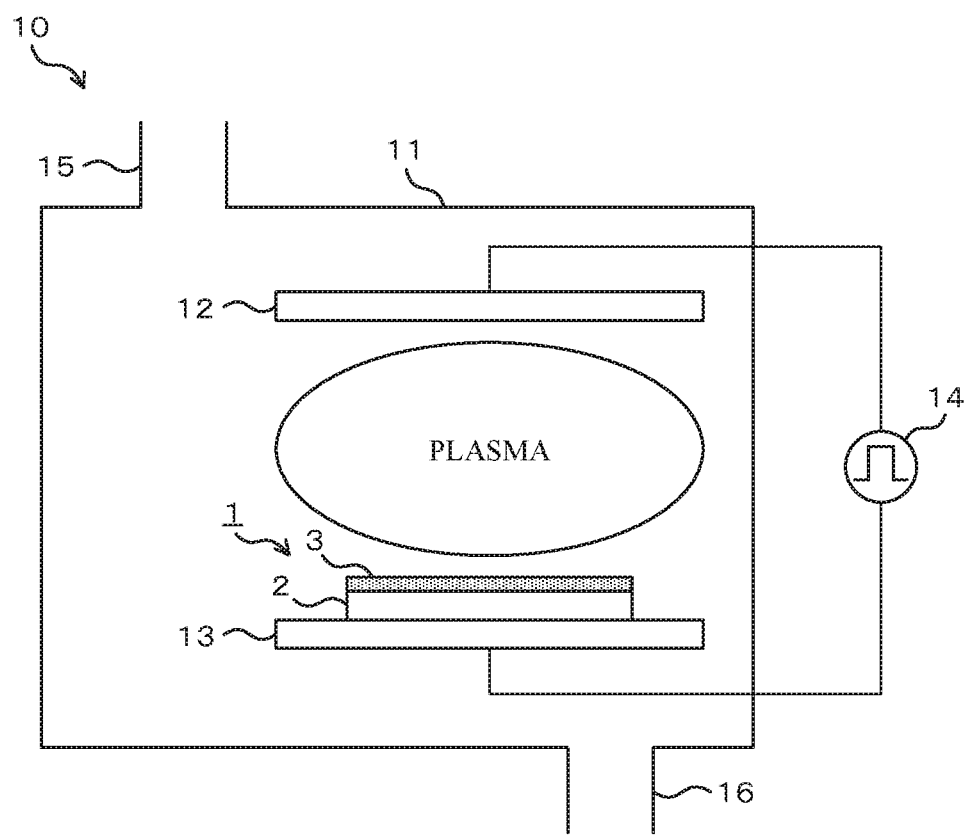
FIG. 1 A schematic view illustrating a configuration of a film formation apparatus for a vanadium nitride film according to an embodiment of the present invention.

Hereinafter, an embodiment of the present invention will be explained referring to the drawings. Note that in this specification and the drawings, the same codes are given to components having substantially the same functional configurations to omit duplicated explanation.

In this embodiment, a plasma chemical vapor deposition method (a so-called plasma CVD method) is used to form a vanadium nitride film composed of a compound containing, as main components, vanadium and nitrogen on the surface of a base material. More specifically, a vanadium nitride film is formed which has a ratio between a vanadium element concentration [at %] and a nitrogen element concentration [at %] in the film of 1.08 or more. Note that though die steel such as SKD11, other tool steel or the like is used as the base material, but the base material is not limited to these materials. Any material may be adopted as the base material as long as it requires a hard coating treatment according to the strength inherent to the material and usage and so on.

In this embodiment, as a film formation apparatus for forming a vanadium nitride film, a plasma processing apparatus 10 as illustrated in FIG. 1 is used. The plasma processing apparatus 10 includes a chamber 11 into which a base material 2 is carried in, an anode 12 and a cathode 13, and a pulse power supply 14. A gas supply pipe 15 from which a raw material gas is supplied is connected to an upper part of the chamber 11, and a gas exhaust pipe 16 which exhausts gas in the chamber is connected to a lower part of the chamber 11. On the downstream side of the gas exhaust pipe 16, a vacuum pump (not illustrated) is provided. The cathode 13 also has a role as a support table which supports the base material 2, and the base material 2 carried in the chamber is mounted on the cathode. Further, inside the chamber 11, a heater (not illustrated) is provided, so that the heater adjusts an atmospheric temperature in the chamber and thereby adjusts the temperature of the base material 2.

Note that the configuration of the plasma processing apparatus 10 is not limited to the one explained in this embodiment. For example, a high-frequency power source may be used in place of the pulse power supply 14, or a shower head which supplies the raw material gas may be provided and used as the anode 12. Further, the base material 2 may be heated only with glow current without providing the heater. In short, the plasma processing apparatus 10 only needs to have a structure capable of converting the raw material gas supplied in the chamber into plasma and form the vanadium nitride film 3 on the base material 2 so as to manufacture a member coated with a vanadium nitride film 1.

Next, a method for manufacturing the member coated with a vanadium nitride film 1 will be explained.

<Film Formation Processing Preparation>

First of all, the base material 2 is carried into the chamber 11 and the base material 2 is set at a predetermined position. Thereafter, evacuation is performed so that the pressure in the chamber becomes, for example, 10 Pa or less. In this event, the temperature in the chamber is about room temperature. Subsequently, the heater is operated to perform a baking treatment on the base material 2. Thereafter, the heater is turned off once, and the plasma processing apparatus 10 is let stand for a predetermined time.

<Heating Step>

Next, a small amount of hydrogen gas is supplied into the chamber, and the heater is operated again. At this heating process, the temperature of the base material 2 is raised up to near a plasma processing temperature. The pressure in the chamber is maintained, for example, at about 100 Pa. Note that the temperature of the base material 2 may become a factor that affects the amount of vanadium in the film, and therefore one example of a method in adjusting the amount of vanadium in the film can be an adjustment of the temperature of the base material 2. Increasing the temperature of the base material 2 enables an increase in the amount of vanadium in the film.

<Plasma Processing Step>

Subsequently, film formation processing of the vanadium nitride film 3 using the plasma CVD method is performed. In this embodiment, the hydrogen gas is converted into plasma prior to the film formation processing of the vanadium nitride film 3. Specifically, the pulse power supply 14 is operated in a state where the hydrogen gas supplied at the heating step is continuously supplied. Hydrogen radicals generated in this manner reduce an oxidation film on the surface of the base material and clean the surface of the base material 2 before the film formation. Note that the voltage, the frequency, the Duty ratio and so on of the pulse power supply 14 are appropriately set so as to convert the gas supplied in the chamber into plasma.

After converting the hydrogen gas into plasma, a nitrogen gas and an argon gas are further supplied into the chamber into which the hydrogen gas is being supplied. This generates plasma of the hydrogen gas, the nitrogen gas, and the argon gas and thereby can stabilize the glow discharge before the formation of the vanadium nitride film.

Thereafter, as a vanadium source gas, a vanadium chloride gas is further supplied into the chamber. This makes a state where the nitrogen gas, the vanadium chloride gas, the hydrogen gas, and the argon gas as the raw material gas for forming the vanadium nitride film 3 are supplied into the chamber. The ratio of partial pressures of the nitrogen gas, the vanadium chloride gas, the hydrogen gas, and the argon gas is set, for example, to 9-10:0.9-1.2:35-50:0.5-5. Further, the pressure in the chamber is set, for example, to 50 Pa or more and 200 Pa or less. Note that the nitrogen source gas for forming the vanadium nitride film 3 is not limited to the nitrogen gas but may be an ammonia gas. Further, as the vanadium source gas for forming the vanadium nitride film 3, the vanadium chloride gas is used which is likely to decompose. For example, a vanadium tetrachloride gas ($VCl_4$) or a vanadium trichloride oxide ($VOCl_3$) gas is used. It is particularly preferable to use the vanadium tetrachloride gas ($VCl_4$) because the number of elements constituting the gas is smaller and removal of impurities in the vanadium nitride film becomes easier. Further, the vanadium tetrachloride gas ($VCl_4$) is preferable also in terms of being easily available, being liquid at room temperature, and being easy supply as a gas.

When the vanadium chloride gas is supplied into the chamber, the vanadium chloride gas is converted into plasma between the electrodes. The vanadium gas and the nitrogen gas converted into plasma between the electrodes adhere to the base material 2, whereby the vanadium nitride film 3 is formed on the surface of the base material 2. Note that the atmospheric temperature in the chamber in the film formation processing of the vanadium nitride film 3 is preferably 450° C. or higher and 600° C. or lower. The voltage in the film formation processing is preferably 700 V or higher and 1800 V or lower. Further, since a glow current value in plasma generation influences the nitrogen amount in the film, increasing the glow current value enables an increase of the nitrogen amount in the film.

Though the hardness of the vanadium nitride film 3 is different depending on the processing conditions in the film formation processing, the vanadium nitride film 3 having a ratio (V [at %]/N [at %]) of the nitrogen element concentration to the vanadium element concentration in the film becomes 1.08 or more is formed in this embodiment. Note that in the following explanation, the ratio (V [at %]/N [at %]) between the vanadium element concentration and the nitrogen element concentration in the film is expressed as a "VN concentration ratio" in some cases.

As illustrated in later-explained examples, the vanadium nitride film 3 having a VN concentration ratio of 1.08 or more has such a hardness that a Vickers hardness HV converted based on Martens hardness obtained by a nano-indentation method is 2400 or more. In short, the vanadium nitride film 3 is formed with the plasma processing conditions appropriately set so that the VN concentration ratio becomes 1.08 or more using the plasma CVD method, whereby the vanadium nitride film 3 having a hardness which cannot be obtained by the ion-plating method as in the prior art can be obtained. Thus, the member coated with a vanadium nitride film 1 improved in abrasion resistance as compared with the prior art can be obtained. Note that the VN concentration ratio can be controlled by gradually changing, during the film formation processing, at least one of parameters influencing the VN concentration ratio, such as the pressure and the atmospheric temperature in the chamber, the hydrogen gas partial pressure, the nitrogen gas partial pressure, the glow current value and so on in the film formation processing.

The VN concentration ratio is preferably 1.10 or more and more preferably 1.30 or more. This can further improve the hardness of the vanadium nitride film. Further, the upper limit of the VN concentration ratio is preferably 2.5, more preferably 2.0 or less, and furthermore preferably 1.85 or less. The total of the vanadium element concentration and the nitrogen element concentration of the vanadium nitride film is preferably 90 at % or more. Further, the upper limit of the total of the vanadium element concentration and the nitrogen element concentration of the vanadium nitride film is preferably 99 at %. The element concentration of vanadium of the vanadium nitride film is preferably 49.5 at % or more, more preferably 50 at % or more, and furthermore preferably 53 at % or more. Further, the upper limit of the element concentration of vanadium of the vanadium nitride film is preferably 70 at %. The film thickness of the vanadium nitride film is appropriately set according to a product being a film formation object, and a preferable film thickness is 0.5 μm or more and 10 μm or less. A further preferable lower limit of the film thickness is 2 μm.

In the film formation method according to this embodiment, the vanadium chloride gas is used as the vanadium source gas in the film formation of the vanadium nitride film, and therefore chlorine is necessarily contained in the vanadium nitride film, and the lower limit of the chlorine element concentration of the vanadium nitride film is preferably 1 at %. A preferable lower limit of the chlorine element concentration in the film is 1.5 at % and a furthermore preferable lower limit is 2 at %. On the other hand, if chlorine in the film exceeds 5 at %, the vanadium nitride film may have deliquescence and the film may disintegrate under air atmosphere. Therefore, in the film formation of the vanadium nitride film according to this embodiment, the vanadium nitride film is formed so that the chlorine concentration in the film becomes 1 at % or more and 5 at % or less by appropriately setting the plasma processing conditions. In contrast to this, in the film formation method of the vanadium nitride film by the conventional ion plating method, metallic vanadium is used as the vanadium source, so that chlorine is not contained in the film.

Note that the hydrogen gas contained in the raw material gas is likely to combine with chlorine, so that when the hydrogen gas is contained as the raw material gas as in this embodiment, chlorine generated from the vanadium chloride gas combines with hydrogen and becomes likely to be discharged to the outside the system, enabling suppression of mixture of chlorine into the film of the vanadium nitride film 3. As a result, a decrease in hardness of the film due to mixture of a large amount of chlorine into the film can be suppressed. The flow rate of the hydrogen gas is preferably 25 times or more to the flow rate of the vanadium chloride gas. Further, though the argon gas is contained in the raw material gas in this embodiment, supply of the argon gas is not essential. Argon ions of the argon gas ionize other molecules and thereby contribute to stabilization of plasma and improvement in ion density, and therefore the argon gas is preferably supplied as needed.

Further, when the plasma CVD method is used in the film formation processing of the vanadium nitride film 3 as in this embodiment, an apparatus equivalent to the film formation apparatus used in the film formation processing of other than a complicated shape article can be used also in the film formation processing for the complicated shape article. In other words, a film formation apparatus of special specifications for the film formation for the complicated shape article becomes unnecessary, thus enabling reduction of cost accompanying the introduction of the film formation apparatus. Further, even when both of the film formation apparatus of special specifications and the film formation apparatus of ordinary specifications are necessary in the conventional film formation method, the film formation apparatus of special specifications becomes unnecessary according to the film formation method of this embodiment, thus enabling reduction in the number of film formation apparatuses to be installed in a factory. This can increase the degree of freedom of the facility layout in the factory.

Further, the vanadium nitride film 3 in this embodiment is a film having a Vickers hardness HV of 2400 or more and a complex elastic modulus of 400 GPa or less. Normally, the hardness and the complex elastic modulus are in a proportional relation, and the complex elastic modulus generally increases with an increase in hardness. However, the vanadium nitride film 3 in this embodiment has a complex elastic modulus suppressed to 400 GPa or less though a Vickers hardness HV reaches 2400 or more. This is a low complex elastic modulus even compared with the film having the same level of hardness and means that an elastically deformed region is wide. More specifically, the vanadium nitride film 3 in this embodiment has high abrasion resistance relative to the film having the same level of hardness. Accordingly, the member coated with a vanadium nitride film 1 in this embodiment coated with such a vanadium nitride film 3 is a member achieving both the hardness and the complex elastic modulus at high levels and has more excellent abrasion resistance than the conventional one. Note that in the case where the VN concentration ratio is in a range of 1.30 to 1.85, both of a hardness of HV of 2900 or more and a complex elastic modulus of 350 GPa or less can be achieved.

While the embodiment of the present invention has been described, the present invention is not limited to the example. It should be understood that various change examples and modification examples are readily apparent to those skilled in the art within the technical spirit as set forth in claims, and those should also be covered by the technical scope of the present invention.

Figure 2:
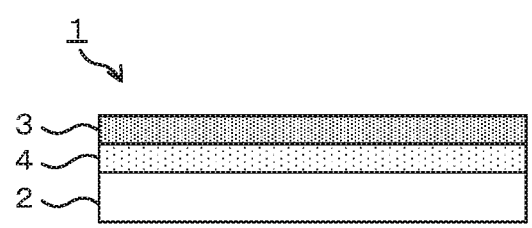
FIG. 2 A schematic view illustrating a film structure of a member coated with a vanadium nitride film according to another embodiment of the present invention.
Figure 3:
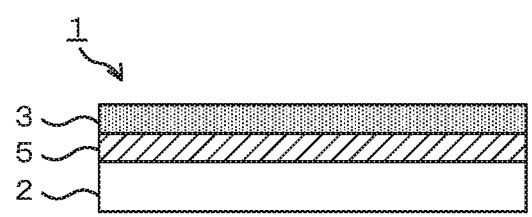
FIG. 3 A schematic view illustrating a film structure of a member coated with a vanadium nitride film according to another embodiment of the present invention.

For example, though the vanadium nitride film 3 is formed on the surface of the base material 2 in the above embodiment, a vanadium nitride film 4 having a VN concentration ratio in the film of 0.70 or more and less than 1.08 may be formed on the surface of the base material 2 and a vanadium nitride film 3 having a VN concentration ratio of 1.08 or more may be formed on the surface of the vanadium nitride film 4 as illustrated in FIG. 2. The vanadium nitride film 4 having a VN concentration ratio of 0.70 or more and less than 1.08 is a film softer than the vanadium nitride film 3 having a VN concentration ratio of 1.08 or more but is a film harder than the base material 2. The vanadium nitride film 4 having a VN concentration ratio of 0.70 or more and less than 1.08 formed as described above can suppress a rapid change in hardness between the vanadium nitride film 3 having a VN concentration ratio of 1.08 or more and the base material 2. This decreases the difference between the films and thereby can improve the adhesion between the films. In this specification, the vanadium nitride film 4 having a VN concentration ratio of 0.70 or more and less than 1.08 is called a "buffer film".

Further, as another embodiment, a concentration gradient film 5 which gradually increases in VN concentration ratio in a range of 0.70 to 1.08 from the base material side toward the vanadium nitride film side may be formed between the base material 2 and the vanadium nitride film 3. Also in the case where the concentration gradient film 5 is formed, the adhesion at the interface between the films increases to make the vanadium nitride film 3 hard to peel off from the base material 2. Note that for formation of the concentration gradient film 5 of vanadium and nitrogen on the surface of the base material 2, it is only necessary to gradually change, during the film formation processing, at least one of the parameters influencing the VN concentration ratio, such as the pressure and the atmospheric temperature in the chamber, the hydrogen gas partial pressure, the nitrogen gas partial pressure, the glow current value and so on in the film formation processing.

EXAMPLES

The vanadium nitride film (VN film) was formed on the surface of the base material using the plasma CVD method, and the hardness of the vanadium nitride film was evaluated.

As the base material on which the vanadium nitride film was formed, the one was used which was obtained by performing quenching and tempering treatments on a round bar of φ22 composed of SKD11 being one kind of the die steel and then cutting the round bar at an interval of 6 to 7 mm, and performing mirror polishing on the surface of each cut member. Note that the vanadium nitride film was formed on a surface on the side subjected to the mirror polishing of the base material. The film formation apparatus having the structure illustrated in FIG. 1 was used, and the pulse power supply was used as the power supply. A series of processing conditions until the film formation processing are listed in following Table 1.

TABLE 1

PROCESSING CONDITIONS (EXAMPLE 1)

| | STEP | | | | | | |
|---|---|---|---|---|---|---|---|
| | EVACUATION | BAKING | COOLING | HEATER TEMPERATURE UP | $H_2$ PLASMA | $H_2 + N_2 +$ Ar PLASMA | VN FILM FORMATION |
| HEATER SETTING TEMPERATURE (° C.) | HEATER OFF | 200 | HEATER OFF | 485 | 485 | 485 | 485 |
| PRESSURE (Pa) | DOWN TO 10 Pa | NOT CONTROLLED | NOT CONTROLLED | 100 | 100 | 58 | 58 |
| $H_2$ FLOW RATE (ml/min) | 0 | 5 | 5 | 100 | 100 | 200 | 200 |
| $N_2$ FLOW RATE (ml/min) | 0 | 0 | 0 | 0 | 0 | 50 | 50 |
| $VCl_4$ FLOW RATE (seem) | 0 | 0 | 0 | 0 | 0 | 0 | 5.1 |
| Ar FLOW RATE (ml/min) | 0 | 0 | 0 | 0 | 0 | 5 | 5 |
| VOLTAGE OF PULSE POWER SUPPLY (V) | 0 | 0 | 0 | 0 | 800 | 1100 | 1500 |
| FREQUENCY OF PULSE POWER SUPPLY (kHz) | 0 | 0 | 0 | 0 | 25 | 25 | 25 |
| DUTY RATIO (%) | 0 | 0 | 0 | 0 | 30 | 30 | 30 |
| OUTPUT FORM | 0 | 0 | 0 | 0 | UNIPOLAR | UNIPOLAR | UNIPOLAR |
| PROCESSING TIME (min) | 30 | 10 | 30 | 30 | 20 | 20 | 180 |

Concrete explanation is as follows.

<Film Formation Processing Preparation>

First of all, the base material is set in the chamber of the film formation apparatus, the chamber is evacuated for 30 minutes to reduce the pressure in the chamber down to 10 Pa or less. In this event, the heater is not operated. Note that the heater is provided inside the chamber, and the atmospheric temperature in the chamber is being measured by a sheathed thermocouple. Subsequently, the setting temperature of the heater is set to 200° C. and a baking treatment is performed on the base material for 10 minutes. Thereafter, the heater is turned off, and the film formation apparatus is let stand for 30 minutes to cool the inside of the chamber.

<Heating Step>

Next, the hydrogen gas is supplied at a flow rate of 100 ml/min into the chamber and the exhaust rate is adjusted to set the pressure in the chamber to 100 Pa. Then, the setting temperature of the heater is set to 485° C. and the base material is heated for 30 minutes. This heating step raises the temperature of the base material up to near the plasma processing temperature.

<Plasma Processing Step>

Next, the pulse power supply is operated at a voltage: 800 V, a frequency: 25 kHz, a Duty ratio: 30%, and a unipolar output form. This converts the hydrogen gas into plasma between the electrodes in the chamber. Thereafter, the flow rate of the hydrogen gas is increased to 200 ml/min and the nitrogen gas and the argon gas are supplied into the chamber. Then, the voltage of the pulse power supply is raised to 1100 V. This makes the hydrogen gas, the nitrogen gas, and the argon gas into a plasma state between the electrodes. Note that the flow rate of the nitrogen gas in this event is set to 50 ml/min and the flow rate of the argon gas is set to 5 ml/min. Further, the exhaust rate is adjusted to set the pressure in the chamber to 58 Pa.

Subsequently, the vanadium tetrachloride gas is supplied into the chamber and the voltage of the pulse power supply is raised to 1500 V. This decomposes the vanadium tetrachloride gas into vanadium and chlorine. Then, vanadium and nitrogen converted into plasma adhere to the base material, whereby a vanadium nitride film is formed on the surface of the base material. This state is maintained for 180 minutes.

Through the above steps, a test piece in which the vanadium nitride film is formed on the surface of the base material is obtained. In this example, other than this test piece, a plurality of test pieces in Examples 2 to 5 and Comparative Examples 1 to 2 which were produced with the processing conditions at start of the supply of the vanadium tetrachloride gas into the chamber, namely, the processing conditions in the film formation of the vanadium nitride film (film formation processing conditions) changed, were prepared. The film formation processing conditions are listed in following Table 2. Note that the processing conditions from the supply of the vanadium tetrachloride gas into the chamber to the start of the film formation of the vanadium nitride film in Examples and Comparative Examples are the same as the processing conditions listed in above Table 1. Further, the processing conditions in above Table 1 are conditions for manufacturing the test piece in Example 1 listed in following Table 2.

<Hardness Measurement of Vanadium Nitride Film>

On each of the test pieces obtained by the above film formation processing, hardness measurement is performed. The hardness measurement is performed by the nano-indentation method using FISCHER SCOPE (registered trademark) HM2000 manufactured by Fischer Instruments. Specifically, a Vickers indenter is pushed into each test piece with a maximum indentation load set to 10 mN, and an indentation depth is continuously measured. Based on the change in indentation depth, the Martens hardness, and the Vickers hardness converted from the Martens hardness, and the complex elastic modulus are calculated by a measuring device. The calculated Vickers hardness is displayed on a screen of the measuring device, and the numerical value is used as the hardness of the vanadium nitride film at a measurement point. In this example, the Vickers hardnesses at arbitrary 20 points on the surface of the test piece are obtained, and an average value of the obtained hardnesses is recorded as the hardness of the vanadium nitride film.

Note that in pushing the indenter into the test piece, an indentation load propagates to a depth of about 10 times the maximum indentation depth of the indenter in some cases. Therefore, once the propagation of the indentation load reaches the base material of the test piece, the influence of the base material may be included in the result of the hardness measurement. Accordingly, for measuring the real hardness of the vanadium nitride film, it is necessary to satisfy "the film thickness of the vanadium nitride film>the maximum indentation depth of the indenter×10".

<Film Thickness Measurement>

Hence, whether the influence of the base material is included in the measured hardness of the vanadium nitride film is evaluated also in this example. The film thickness of the vanadium nitride film is measured by vertically cutting the test piece and subjecting the cut surface to mirror polishing, then observing the cut surface under a metallurgical microscope set at 1000-fold magnification, and performing calculation based on the observed image information.

<Composition Analysis of Vanadium Nitride Film>

Next, the composition of the vanadium nitride film of each test piece was analyzed. The analysis conditions are as follows.

EPMA: JXA-8530F manufactured by JEOL Ltd.
Measurement mode: semiquantitative analysis
Acceleration voltage: 15 kV
Irradiation current: $1.0 \times 10^{-7}$ A
Beam shape: spot

TABLE 2

| | | EXAMPLE 1 | EXAMPLE 2 | EXAMPLE 3 | EXAMPLE 4 | EXAMPLE 5 | COMPARATIVE EXAMPLE 1 | COMPARATIVE EXAMPLE 2 |
|---|---|---|---|---|---|---|---|---|
| VN FILM FORMATION CONDITIONS | HEATER SETTING TEMPERATURE (° C.) | 485 | 485 | 485 | 520 | 550 | 485 | 485 |
| | PRESSURE (Pa) | 58 | 58 | 58 | 58 | 58 | 58 | 58 |
| | H$_2$ FLOW RATE (ml/min) | 200 | 200 | 200 | 20C | 200 | 200 | 200 |
| | N$_2$ FLOW RATE (ml/min) | 50 | 50 | 50 | 50 | 50 | 50 | 50 |
| | VCl$_4$ FLOW RATE (seem) | 5.1 | 4.8 | 4.7 | 4.7 | 4.7 | 3.1 | 4.1 |
| | Ar FLOW RATE (ml/min) | 5 | 5 | 5 | 5 | 5 | 5 | 5 |
| | VOLTAGE OF PULSE POWER SUPPLY (V) | 1500 | 1500 | 1500 | 150 | 1500 | 1500 | 1500 |
| | FREQUENCY OF PULSE POWER SUPPLY (kHz) | 25 | 25 | 25 | 25 | 25 | 25 | 25 |
| | DUTY RATIO (%) | 30 | 30 | 30 | 30 | 30 | 30 | 30 |
| | OUTPUT FORM | UNIPOLAR | UNIPOLAR | UNIPOLAR | UNIPOLAR | UNIPOLAR | UNIPOLAR | UNIPOLAR |
| | PROCESSING TIME (min) | 180 | 180 | 180 | 180 | 180 | 180 | 360 |

Beam diameter set value: 0
Dispersive crystal: LDE6H, TAP, LDE5H, PETH, LIFH, LDE1H <Measurement Result>

The Vickers hardness, the complex elastic modulus, the film thickness and the composition of the vanadium nitride film measured in the above procedure are listed in following Table 3.

According to the results of the above examples, it is found that when the VN concentration ratio is 1.08 or more, the hardness can be increased to improve the abrasion resistance. For increasing the hardness and decreasing the complex elastic modulus to further improve the abrasion resistance, the VN concentration ratio is preferably 1.30 to 1.85.

Note that the thickness of the vanadium nitride film of each test piece is a thickness greatly exceeding 10 times the

TABLE 3

| | | EXAMPLE 1 | EXAMPLE 2 | EXAMPLE 3 | EXAMPLE 4 | EXAMPLE 5 | COMPARATIVE EXAMPLE 1 | COMPARATIVE EXAMPLE 2 |
|---|---|---|---|---|---|---|---|---|
| HARDNESS OF VN FILM (HV) | | 2989 | 2541 | 2525 | 3004 | 2642 | 778 | 1758 |
| COMPLEX ELASTIC MODULUS OF VN FILM (GPa) | | 277 | 327 | 325 | 328 | 383 | 219 | 301 |
| FILM THICKNESS OF VN FILM (μm) | | 3.24 | 3.07 | 3.18 | 3.67 | 3.49 | 3.39 | 5.52 |
| MAXIMUM INDENTATION DEPTH AT HARDNESS MEASUREMENT (μm) | | 0.164 | 0.142 | 0.140 | 0.119 | 0.123 | 0.262 | 0.173 |
| COMPOSITION OF VN FILM | V (at %) | 55.6 | 51.6 | 50.1 | 62.2 | 63.2 | 46.7 | 48.7 |
| | N (at %) | 40.7 | 43.9 | 45.3 | 34.0 | 33.1 | 48.4 | 47.2 |
| | Cl (at %) | 2.2 | 2.7 | 3.1 | 2.1 | 1.8 | 2.7 | 2.6 |
| VN FILM CONCENTRATION RATIO (V/N) | | 1.37 | 1.18 | 1.11 | 1.83 | 1.90 | 0.96 | 1.03 |

As listed in Table 3, the test pieces in Examples 1 to 5 have a hardness of exceeding HV 2500. In other words, according to the present invention, a film harder than the vanadium nitride film having a hardness of about HV 2300 as in the prior art can be obtained. Further, as listed in Table 3, the vanadium nitride film contains larger amounts of vanadium and nitrogen as main elements in the film and contains a next larger amount of chlorine. Here focusing attention on the VN concentration ratio (V [at %]/N [at %]) in the film, the values of the VN concentration ratio of Examples 1 to 5 are generally larger than the values of the VN concentration ratio of Comparative Examples. Taking this result and the result of hardness measurement of the vanadium nitride film into consideration, it is found that when the VN concentration ratio is a fixed value or more, the hardness of the vanadium nitride film improves. More specifically, when the VN concentration ratio of the vanadium nitride film is 1.08 or more, the vanadium nitride film of an HV 2400 or more which cannot be achieved by the conventional method can be obtained.

Figure 4:
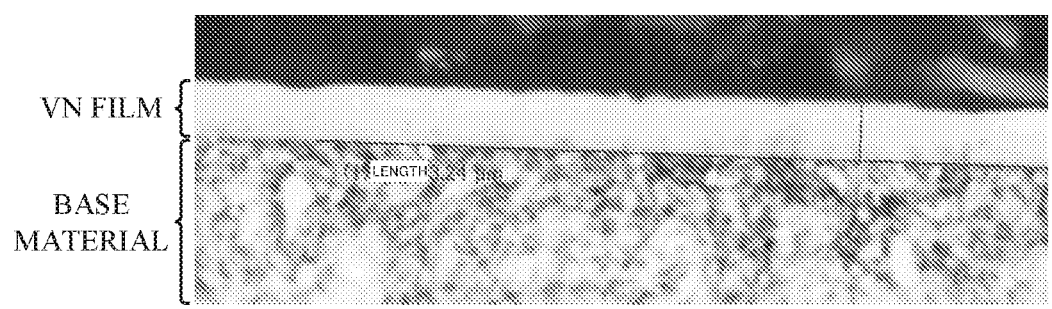
FIG. 4 A cross-sectional image of a test piece in Example 1 observed under a metallurgical microscope.

Further, the test pieces in Examples 1 to 5 have excellent characteristics such as a complex elastic modulus of the vanadium nitride film of 400 GPa or less. In particular, focusing attention on Examples 1 and Example 2, the vanadium nitride film in Example 1 decreases in complex elastic modulus though its hardness increases with respect to the vanadium nitride film in Example 2. More specifically, the vanadium nitride film in Example 1 is harder and has a wider elastically deformed region than the vanadium nitride film in Example 2 and thereby greatly improves in abrasion resistance. Besides, focusing attention on Example 4 and Example 5, the vanadium nitride film in Example 4 decreases in complex elastic modulus though its hardness increases with respect to the vanadium nitride film in Example 5. More specifically, the vanadium nitride film in Example 4 is harder and has a wider elastically deformed region than the vanadium nitride film in Example 5 and thereby greatly improves in abrasion resistance.

maximum indentation depth of the indenter at the hardness measurement as listed in Table 3, and therefore it can be said that the hardness of the vanadium nitride film listed in Table 3 is a numerical value not influenced by the base material. Further, as is found from the cross-sectional image of the test piece in Example 1 illustrated in FIG. 4, the vanadium nitride film is uniformly formed on the entire surface of the base material, so that it is estimated that the film thickness at an arbitrary point of the test piece becomes almost equivalent value to the film thickness measurement result listed in Table 3. Therefore, it is found that the measurement result at a part that receives influence of the hardness of the base material is not included in the measurement results of the hardnesses at arbitrary 20 points. In short, the hardness of the vanadium nitride film listed in Table 3 is the hardness of the film itself.

Note that when the film thickness of the vanadium nitride film to be formed on the surface of the base material is 1 μm or less, the measurement result of EPMA includes the influence of the composition of components of the base material. Therefore, in the case of calculating the VN concentration ratio of a vanadium nitride film having a small film thickness, it is necessary to perform EPMA measurement of only the base material in advance and subtract the vanadium concentration and the nitrogen concentration derived from the base material from the measurement result of EPMA after the film formation of the vanadium nitride film.

INDUSTRIAL APPLICABILITY

The present invention is applicable to hard coating treatment of a die, a tool and so on.

EXPLANATION OF CODES 1 member coated with a vanadium nitride film
2 base material 3 vanadium nitride film
4 buffer film
5 concentration gradient film
10 plasma processing apparatus
11 chamber
12 anode
13 cathode
14 pulse power supply
15 gas supply pipe
16 gas exhaust pipe

The invention claimed is:

1. A vanadium nitride film formed on a surface of a base material,
 wherein a ratio V [at %]/N [at %] between a vanadium element concentration and a nitrogen element concentration in the film is 1.08 or more and a chlorine element concentration in the film is 1 at % or more and 5 at % or less; and
 wherein a total of the vanadium element concentration and the nitrogen element concentration is 90 at % or more.

2. The vanadium nitride film according to claim 1,
 wherein the vanadium element concentration is 49.5 at % or more.

3. A member coated with a vanadium nitride film,
 wherein a vanadium nitride film having a ratio V [at %]/N [at %] between a vanadium element concentration and a nitrogen element concentration of 1.08 or more and a chlorine element concentration of 1 at % or more and 5 at % or less is formed on a surface of a base material; and
 wherein a total of the vanadium element concentration and the nitrogen element concentration is 90 at % or more.

4. The member coated with a vanadium nitride film according to claim 3,
 wherein the vanadium element concentration is 49.5 at % or more.

* * * * *